United States Patent [19]

Cochran

[11] Patent Number: 4,773,900
[45] Date of Patent: Sep. 27, 1988

[54] INFUSION DEVICE

[76] Inventor: Ulrich D. Cochran, 11525 Snapper Creek Dr. N., Miami, Fla. 33173

[21] Appl. No.: 898,302

[22] Filed: Aug. 20, 1986

[51] Int. Cl.$^4$ ............................................. A61M 37/00
[52] U.S. Cl. .................................... 604/143; 604/140; 222/389
[58] Field of Search ........ 604/140, 141, 143, 145–150, 604/131, 891, 68, 69, 70, 71, 72; 222/130, 386, 389; 60/533, 583; 92/8, 9, 81, 82, 130 B

[56]  References Cited

U.S. PATENT DOCUMENTS

| | | | |
|---|---|---|---|
| Re. 29,176 | 4/1977 | Loeffler | 222/389 |
| 1,314,468 | 8/1919 | Dunbar | 222/389 |
| 2,547,099 | 4/1951 | Smoot . | |
| 2,865,371 | 12/1958 | Dorbecker . | |
| 3,315,768 | 4/1967 | Stuhler et al. | 92/9 |
| 4,063,556 | 12/1977 | Thomas et al. | 604/140 |
| 4,132,332 | 1/1979 | Wassilieff | 222/387 |
| 4,180,067 | 12/1979 | Derlien | 604/143 |
| 4,265,241 | 5/1981 | Portner . | |
| 4,335,835 | 6/1982 | Beigler | 222/95 |
| 4,351,335 | 9/1982 | Whitney et al. | 604/143 |
| 4,360,019 | 11/1982 | Portner . | |
| 4,426,022 | 1/1984 | Lang et al. | 222/389 |
| 4,505,710 | 3/1985 | Collins | 604/891 |
| 4,561,856 | 12/1985 | Cochran | 604/143 |

FOREIGN PATENT DOCUMENTS 1046216  4/1966  United Kingdom ............... 222/389

*Primary Examiner*—Stephen C. Pellegrino
*Assistant Examiner*—Ralph Lewis
*Attorney, Agent, or Firm*—Tilton, Fallon, Lungmus

[57]  ABSTRACT

An infusion device for dispensing drugs and other fluids at controlled rates over extended time periods. The device includes a syringe section and a power section that are connected together in use, the power section having a casing defining a first chamber containing a vacuum-stable viscous liquid and a second chamber under partial vacuum. A metering passage extends between the two chambers, and a piston is slidably received in the casing and constitutes a movable wall of the first chamber so that as the viscous liquid gradually flows through the metering passage into the second chamber the piston retracts slowly to cause fluid to be discharged from the syringe.

36 Claims, 2 Drawing Sheets

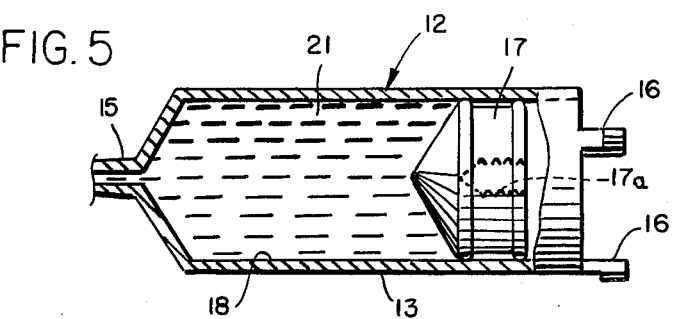
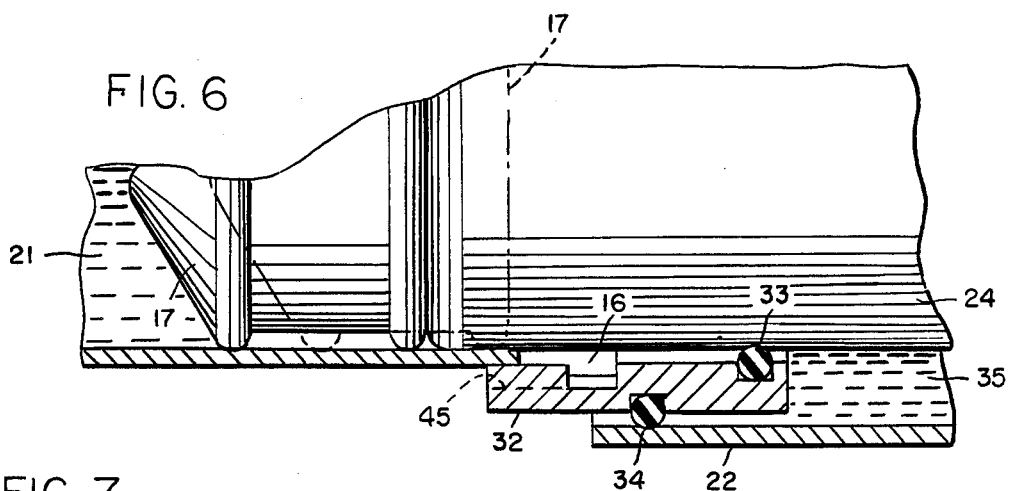
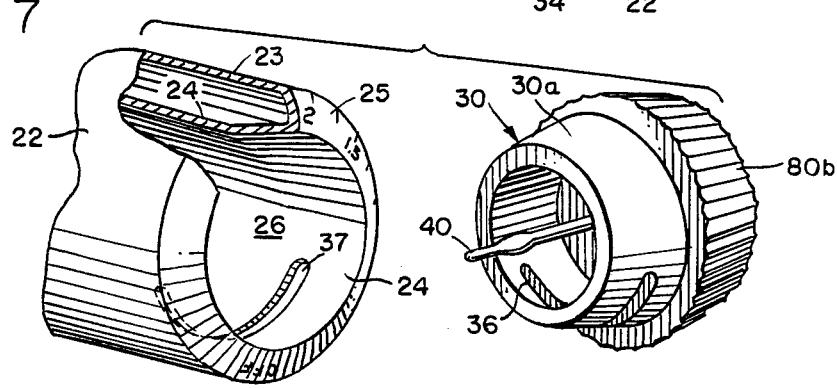
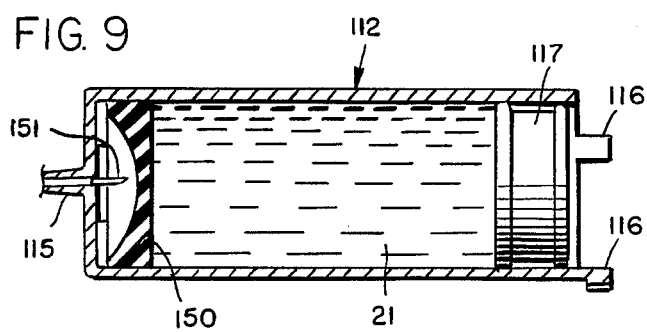
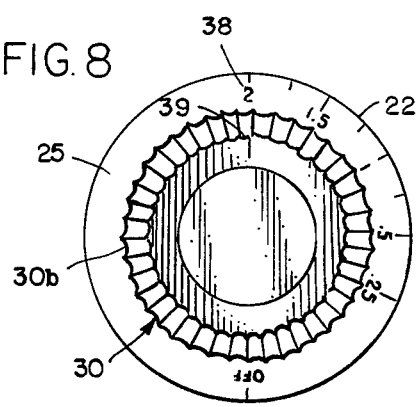

INFUSION DEVICE

BACKGROUND AND SUMMARY

A variety of devices have been disclosed in the medical field for slowly and continuously infusing drug solutions such as heparin, antibiotics, and chemotherapy agents. In one such device, a drug is contained in an elastic balloon reservoir that gradually deflates to deliver the medication through an orifice of selected size. Another device disclosed in U.S. Pat. No. 4,561,856 utilizes a gas spring to drive a syringe piston and cause liquid to be discharged from a syringe section. U.S. Pat. No. 4,180,067 describes a vacuum cylinder and a flow-restricting valve as the driving means for forcing fluid from a container at a controlled rate. Other patents, such as U.S. Pat. No. 4,265,241, show devices in which a pressure differential is created by pressurizing one chamber and then allowing the gas to pass into another chamber, equalizing pressures and shifting a piston as such equalization occurs (FIG. 5). U.S. Pat. Nos. 4,335,835, 4,360,019, 2,547,099, and 2,865,371 disclose variations of pressure delivery systems. U.S. Pat. No. 4,505,710 (FIG. 1) shows a membrane that serves as a one-way metering valve through which liquid flows under pressure into a receiving chamber. As the receiving chamber expands, a drug in an adjacent chamber is slowly expelled for delivery to a patient.

All of such prior devices are believed to have major shortcomings or disadvantages. In some cases, flow rate is determined by the passage of a drug through an orifice and, therefore, flow rate is dependent on the particular viscosity of the drug to be delivered. Other devices are relatively difficult to fill, or are designed so that flow rate cannot be readily adjusted by a physician, or utilize membranes and other components that may not be compatible with certain types of drugs, or are relatively complex and expensive in construction, or, in the case of operative failure, tend to deliver a drug at an increased (rather than decreased) dosage rate.

The present invention is directed to a relatively simple and reliable device for delivering a drug at a rate that may be readily controlled by a physician and is independent of the viscosity of the particular drug to be infused. The device is easily filled (in essentially the same manner as a standard syringe), has no greater problems of drug compatibility than standard syringes, and may be filled either during manufacture or at the time of use. The power module uses a vacuum chamber and, in the event of accidental or unintended vacuum loss, the rate of drug delivered to the patient decreases rather than increases. In a preferred embodiment, vacuum loss is also visually and easily detectable by means of a vacuum loss indicator.

Briefly, the device comprises a syringe section and a power section. The power section includes a casing having a first chamber containing a viscous liquid and a second chamber under partial vacuum. A piston is slidably received in the casing and constitutes a movable wall of the first chamber. That piston is connected to the syringe section in such a way that retraction of the piston causes displacement of the syringe plunger. In use of the device, a metering passage between the two chambers is opened to allow the viscous fluid to flow into the evacuated second chamber. As the volume of viscous liquid in the first chamber is reduced, the piston of the power section retracts to drive the plunger of the syringe section forwardly, thereby dispensing the drug from the syringe at a predetermined rate.

In a preferred embodiment, the two sections comprise separate modules that are either connected together at the time of manufacture or immediately prior to use. The latter is feasible because, among other things, operation of the power module is not dependent on drug viscosity and, therefore, the same power module might be connected to any of a variety of syringe modules containing different drugs. Once connected, the two modules are constructed to prevent or resist separation, thereby precluding reuse of the parts. Ideally, during the initial procedure of connecting the two modules together, a bolus of drug is expelled from the syringe to clear the administration line of air. Coupling of the modules thereby arms the device for immediate use despite the fact that subsequent administration of drug will occur at a reduced rate of flow. The particular rate of flow of the viscous fluid through the metering passage, and hence the rate of administration of the drug delivered by the syringe unit, may either be preset during manufacture or may be set at the time of use by the pharmacist or physician. In the latter case, such adjustment is achieved simply by rotating a valve member provided by the power module into any selected position of adjustment indicated by a delivery-rate scale on that module. Should a later change in delivery rate, or an interruption in drug delivery, be deemed desirable by the physician, such an adjustment may be made by resetting the knob of the valve unit.

While differences in drug viscosity do not significantly alter the delivery rate of the device, substantial changes in the temperature of the viscous fluid of the power unit could have such an effect if it were not for a self-regulating feature incorporated into the system. Where the device is worn continuously in contact with the body the operating temperature would be relatively constant and no such self-regulation is necessary. The self-regulating feature is advantageous where, for example, a patient may wish to detach the device from his (her) body while resting in bed and, under such conditions, the temperature of the device would be significantly lowered. By including in the vacuum chamber a small amount of water or other volatile fluid that is immiscible with the viscous medium, temperature-dependent changes in viscosity of the viscous fluid medium may be substantially offset by changes in the vapor pressure of the regulating fluid, with the result that generally uniform drug delivery rates may be achieved even at different operating temperatures.

Other features, advantages and objects will become apparent from the specification and drawings.

DRAWINGS

FIG. 5 is a side elevational view, shown partly in section, of the syringe module.

FIG. 6 is a fragmentary longitudinal sectional view illustrating the relationship between the power and syringe modules at the beginning and completion of a coupling operation.

FIG. 7 is an exploded perspective view illustrating the relationship between the valve member and the casing of the power module.

FIG. 8 is an end view of the power module showing the adjustable valve therefor.

FIG. 9 illustrates a modified version of the syringe module in longitudinal section.

DETAILED DESCRIPTION OF PREFERRED EMBODIMENTS

Figure 1:
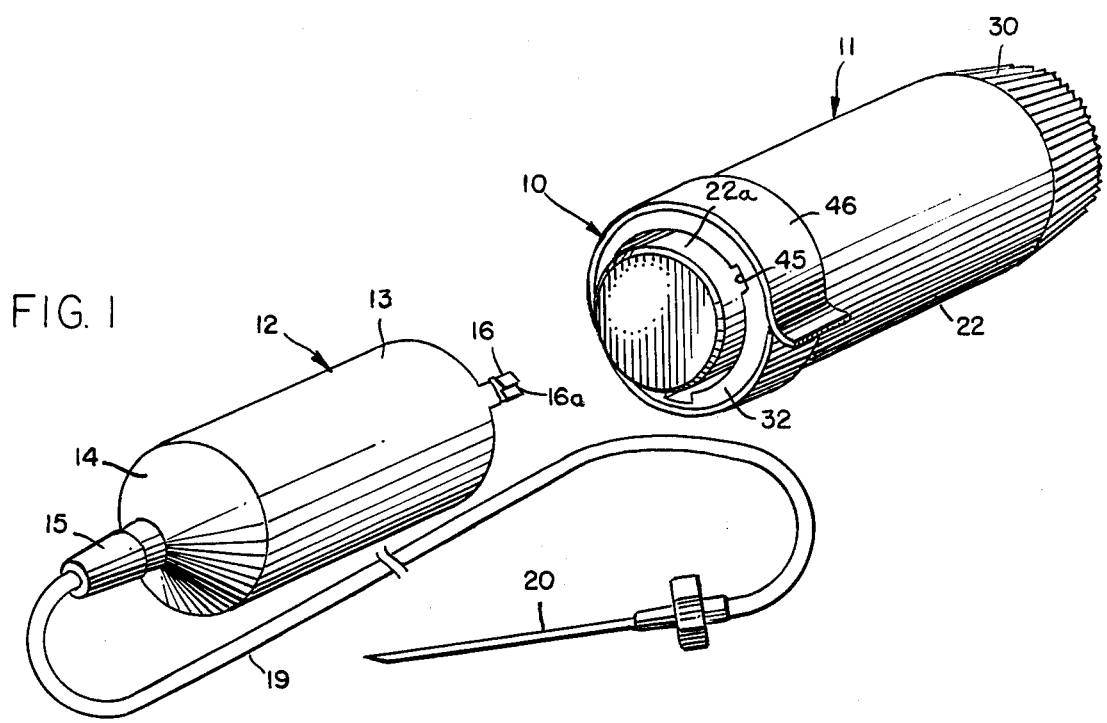
FIG. 1 is a perspective view of a device embodying the present invention, the device being shown with the syringe and power modules in separated condition.

Referring to FIGS. 1-8 of the drawings, the numeral 10 generally designates a drug infusion device having a power section 11 and a syringe or delivery section 12. The two sections might be connected during manufacture so that the assembly is supplied to the user as a single unit; however, one of the advantages of this system is that the same power section 11 might be used with any of a variety of syringe sections 12 containing different drugs. Under such circumstances, the syringe modules would be stored separately, often under refrigeration, and be coupled to power modules by a pharmacist or physician just prior to use. Accordingly, FIG. 1 depicts the two sections as separate modules which may be joined together to produce the assembled device of FIG. 2.

The syringe unit 12 includes a syringe barrel 13 of cylindrical shape having an end wall 14 terminating in neck 15 having a discharge passage 15a therethrough. The barrel is open at its opposite end 13a and is provided with a plurality of axially projecting lugs 16 for coupling the syringe unit 12 to power unit 11. A plunger 17 formed of rubber or any other suitable elastomeric material is slidably received within the chamber 18 of the barrel and closes off the barrel's open end 13a.

Neck 15 may be permanently connected to one end of a flexible delivery tube 19, the opposite end of the tube being provided with a connection to a suitable injection needle 20 that would normally be covered by a sterile cap or cover (not shown). The connection between delivery tube 19 and neck 15 may be a permanent one made during manufacture. Alternatively, neck 15 may be provided with its own sterile cap (not shown) which, upon removal, may then be connected by the user to the delivery tube. In the latter case, the connection between neck 15 and tube 19 might be non-detachable; that is, a user having once connected the parts together would be unable to disassemble them, at least without rendering the syringe assembly inoperative.

Within chamber 18 of the syringe module is a suitable drug 21 in liquid form. The drug or injection fluid may be heparin, an antibiotic, a chemotherapy agent, or any of a variety of other injectable medical preparations. The composition of such a preparation has no direct bearing on this invention except to the extent that it is an injectable therapeutic solution that is intended to be administered over a protracted period, usually continuously, and at a predetermined flow rate.

The power module 11 includes a generally cylindrical casing 22 that has outer and inner concentric walls 23 and 24 joined at the distal end of the casing by integral end wall 25. Inner wall 24 defines an inner chamber 26 that is closed at its proximal end by end wall 27. As shown in the drawings, the inner wall extends in a proximal direction beyond outer wall 23 and is dimensioned to be received within the open end 13a of syringe module 12 where it directly engages syringe plunger 17 and functions as the contact member for driving or advancing that plunger.

The opposite or distal end of the inner chamber 26 is sealed by a closure member 30 which also functions as a valve element and as a vacuum-loss indicator. Ideally, the inner wall 24 flares outwardly to a slight extent near the distal end of the casing and the insert portion 30a of closure member 30 is of slightly tapered or frusto-conical shape to seal tightly against the flared surfaces of the wall. The closure member also includes an enlarged external portion that bears against end wall 25 and, as shown in the drawings, may be ribbed or knurled along its outer surface so that an operator may grip or rotate the closure member in relation to casing 22. Alternatively, the closure member may be provided with one or more openings for receiving the projection or projections of a suitable wrench or tool (not shown) required for rotatably adjusting that member.

Figure 2:
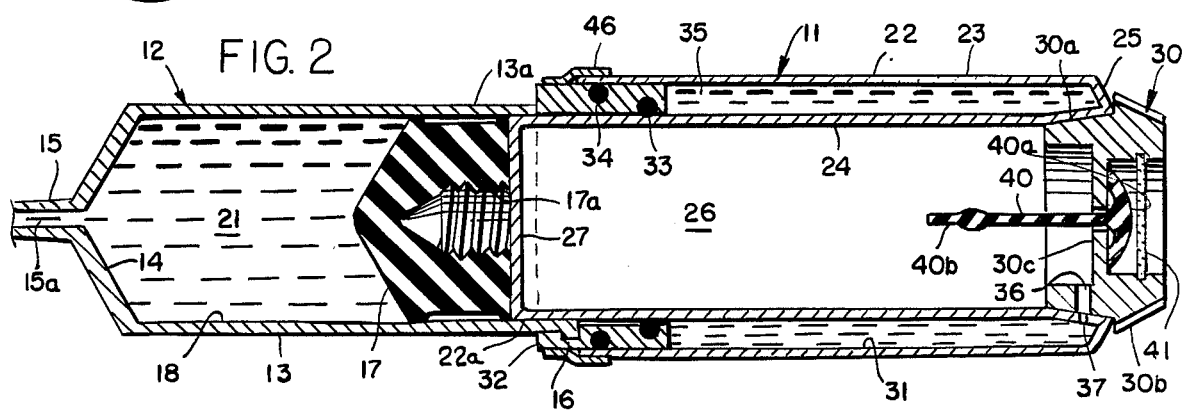
FIG. 2 is a longitudinal sectional view of the device with the syringe and power modules in connected condition.

Referring to FIGS. 2, 6 and 7, casing 22 also defines an annular outer chamber 31 concentric with inner chamber 26. At its proximal end, the outer chamber is closed by a slidable annular piston 32. If the piston is formed of relatively rigid material, inner and outer O-rings 33 and 34 may be supported within grooves of the piston for slidably and sealingly engaging the outer surface of inner wall 24 and the inner surface of outer wall 23. It will be understood that the annular piston 32 may itself be formed of flexible and resilient material so that integral ribs or sealing elements may be substituted for separate O-rings 33 and 34.

The annular outer chamber 31 is filled with a viscous fluid 35. While such a material may be semi-solid in appearance, it must nevertheless be a true fluid in the sense that it must be capable of flowing at some rate under operating temperatures (within the broad range of approximately 15° to 40° C.) and operating pressure conditions. Also, the fluid must be vacuum stable; that is, it must not boil or volatilize in a vacuum at temperatures below 40° C. Any of a variety of highly viscous vacuum-stable fluid media, or blends of such media, may be used, including viscous silicone fluids, dilatant silicone compounds (Dow Corning, Midland, Michigan), oils, greases, and the like. A particularly effective viscous fluid medium is polyisobutylene. While such materials are too viscous to be measured by standard viscosity tests, the change in polyisobutylenes from viscous liquids (semi-solids) to elastic solids occurs over a molecular weight range of approximately 15,000 to 30,000 (Staudinger). Effective results have been achieved using LM grade polyisobutylenes having viscosity average molecular weights (Staudinger) within the range of 8,700 to 17,000, such polyisobutylenes being marketed under the "Vistanex" trademark by Exxon Corporation.

As shown in FIGS. 2 and 7, closure member 30 has an opening 36. A corresponding opening 37 is formed in the inner wall 24 of casing 22. When the two openings are in communication with each other, they form a metering passage for the flow of viscous fluid 35 from outer chamber 31 into inner chamber 26. The two openings may take the form of circumferentially-elongated slots so that as the closure/valve member 30 is rotated the size of the metering passage is progressively increased or diminished. If desired, one of the slots may be replaced by a series of discrete openings so that rotation of member 30 results in a limited number of predetermined incremental changes in the size of the metering passage. Appropriate indicia 38, including scale markings, may be provided on end wall 25 of the casing, and the closure/valve member 30 may be provided with a suitable index mark 39 (FIG. 8), to facilitate adjustment of member 30 between an "off" position, in which flow of fluid through the adjustable metering passage is blocked, and any of a series of selected "open" positions. One of the openings 36 or 37 may be tapered so that the changes in rate of flow are non-linear in relation to the extent of angular adjustment of the enlarged knob portion 30b of member 30.

Inner chamber 26 is a vacuum chamber. That vacuum is described as a "partial vacuum" herein only because an absolute vacuum is unattainable; the extent of evacuation should be high with pressures reduced to the range of approximately 1 to 5 millimeters of mercury. However, where the drug delivery device is expected to be used over a substantial range of temperatures (within the general operating range of 15° to 40° C.), it may be desirable to "contaminate" the vacuum with a small amount of water or other volatile fluid that generates progressively increasing vapor pressures with increasing temperatures over the operating range and that is totally immiscible in the viscous medium 35. The vapor pressure of the volatile fluid thereby tends to offset the effects of decreasing viscosity of medium 35 a temperatures increase. Conversely, as temperatures are reduced and viscosity increases, the vapor pressure of the volatile medium decreases so that the net external pressure on the viscous medium is increased to maintain a substantially uniform rate of flow despite the reduction in temperature. It is believed apparent that the advantages of providing such self-regulation to compensate for changes in viscosity of medium 35 at different temperatures may not be significant if the drug delivery device is to be used only within a relatively narrow temperature range as, for example, where it is designed to be used only when held in direct contact with a patient's body.

The closure member 30 may be provided with indicating means for signaling if for any reason the vacuum seal for inner chamber 26 is broken. In the embodiment illustrated, such indicating means takes the form of a resilient elastic sealing member 40 having an enlarged head portion 40a and an integral stem portion 40b. The stem extends through an aperture in wall or partition 30c of closure member 30 and simply serves as retention means for the resilient head portion. When the vacuum within chamber 26 is intact, member 40 assumes the configuration depicted in FIG. 2 with the head portion 40a deformed and urged into tight sealing engagement with the partition. Should the vacuum in chamber 26 be lost, head portion 40a expands axially into an enlarged condition so that its rounded outer surface engages transparent (or translucent) panel 41 carried by the closure member. Such contact between head portion 40c and panel 41 is readily apparent from an external examination of the power unit, thus providing a reliable indication that leakage or vacuum loss has occurred.

The power and syringe sections 11 and 12 may be joined together during manufacture and sold as an assembled unit with the syringe chamber 18 being pre-filled with a suitable drug. However, one of the advantages of the system lies in the fact that the power unit operates essentially the same way, at a selected infusion rate, regardless of the viscosity of drug 21. It therefore becomes highly advantageous to manufacture the power and syringe sections as separate modules. The physician, pharmacist, or nurse may readily connect a power module 11 to any of a variety of syringe modules containing different drugs knowing that the particular viscosity of any of such drugs will not significantly affect the operation of the power unit.

FIG. 1 illustrates a two-unit device as it might appear just prior to coupling of the modules. The protruding end portion 22a of the casing 22 defining the inner chamber 26 is inserted into the cavity 29 of plunger 17, the three lugs 16 of the syringe barrel are inserted into bayonet slots 45 of annular piston 32, and the two modules are rotated to drive the lugs along the full length of the slots. As shown most clearly in FIGS. 1 and 3, each lug 16 and bayonet slot 45 has ratchet teeth 16a and 45a, respectively, to prevent reverse or retrograde rotation of the parts. If desired, a tape band 46 may be provided over the adjacent surfaces of outer casing wall 23 and annnular piston 32 to securely anchor the piston against rotation within the casing as the syringe module is being coupled to the piston. Also, the strippable adhesive band helps insure against the possibility of creeping action of the piston during storage and handling. It has been found, however, that where the fluid medium 35 is polyisobutylene or some other highly viscous fluid medium, problems of rotation of piston 32 during a coupling operation, and creep of the piston during handling and storage, are not significant even if adhesive strip 46 is omitted.

Figure 3:
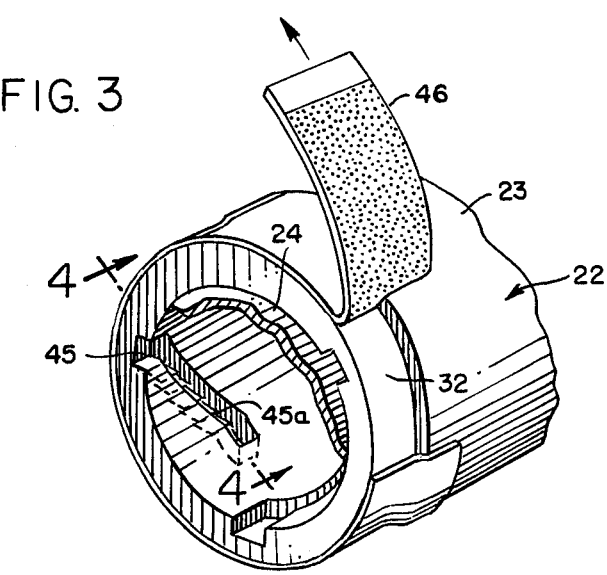
FIG. 3 is an enlarged fragmentary perspective view illustrating details of the coupling means for the two modules.
Figure 4:
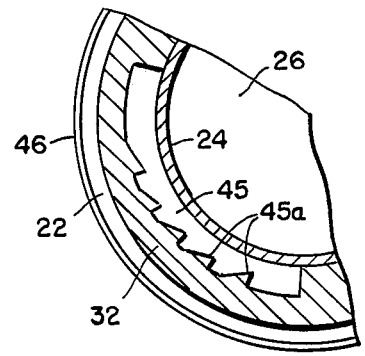
FIG. 4 is a fragmentary sectional view taken along line 4—4 of FIG. 3.

FIG. 5 depicts a syringe module 12 just prior to a coupling operation. In that view, and also in FIG. 6 in broken lines, the syringe plunger 17 is shown in an initial (retracted) state. Advancement of that plunger would cause fluid 21 to be discharged from the chamber 18 into the administration line 19 and needle 20. During the step of coupling the syringe module to the power module, lugs 16 are guided axially as well as circumferentially within slots 45. The act of coupling the two modules together simultaneously advances plunger 17 a short distance from the broken line position into the solid line position of FIG. 6. Such advancement of the plunger drives a bolus of drug from the syringe module and through the administration line 19 and needle 20, thereby clearing the line of air. The adhesive tape strip 46, if used, is then removed as indicated in FIG. 3, the rotary closure/valve member 30 is turned to the desired delivery rate as indicated by indicia 38 and 39, needle 20 is inserted intravascularly or subcutaneously, and the drug delivery device is taped or otherwise secured to the patient. As the viscous fluid 35 is metered slowly into the evacuated chamber 26, the annular piston 32 retracts within the annular outer chamber 31 causing drug 21 to be gradually discharged from syringe module 12. Ordinarily such administration is continuous over a prolonged period that may extend to several days; however, such administration may be interrupted, or the administration rate may be altered, by resetting valve member 30.

While the use of a pre-filled syringe module 12 has been described, it is to be understood that such module might be filled on site in essentially the same manner as a conventional syringe. More specifically, the syringe module might be filled by injecting a drug through the lumen 15a of neck 15, or the drug might be drawn into the syringe by retraction of plunger 17. Threaded opening 17a may be used to attach the threaded end of a suitable retraction tool (not shown), or the plunger may be provided with any other effective gripping means, to facilitate retraction of the plunger for filling the syringe module.

The rate of drug administration is dependent on the size of the metering orifice 36–37 and the viscosity of the fluid medium 35, it being assumed that the extent of evacuation of inner chamber 26 would be constant except for the possible inclusion of a small amount of "contaminating" volatile liquid as previously described. The use of a highly viscous medium such as polyisobutylene is advantageous because, among other things, it permits construction of a delivery system with larger metering openings 36–37 than would be possible if a system of the same delivery rate were to be provided with a medium of lower viscosity. Because of their large size, openings 36 and 37 are relatively easy and inexpensive to form during manufacture. Also, slight variations in size, should they occur, would have far less effect on drug delivery rates.

FIG. 9 depicts an aternative syringe module 112 which couples to a power module in the same manner already described. However, unlike the module shown in FIG. 5, module 112 has an inner diaphragm 150 positioned to be pierced by a needle 151 when the resilient diaphragm is flexed forwardly towards neck 115. Such forward flexing or displacement of the diaphragm occurs when plunger 117 is advanced slightly. As previously described in connection with the first embodiment, such initial advancement of plunger 117 may take place when the lugs 116 are rotated in the slots 45 of the annular piston 32 of the power module. Therefore, in the embodiment of FIG. 9, limited initial advancement of plunger 117 during coupling of the parts first causes piercing of diaphragm 150 followed by the introduction of a bolus of drug 21 into the administration line and needle.

While in the foregoing I have disclosed embodiments of the invention in considerable detail for purposes of illustration, it will be understood by those skilled in the art that many of these details may be varied without departing from the spirit and scope of the invention.

I claim:

1. A power module for a drug infusion device comprising a casing having a first chamber and a second chamber and having a metering flow passage therebetween; adjustable valve means for opening and closing said passage; a piston slidably received in said casing and constituting a movable wall of said first chamber; said second chamber being of constant volume and being under partial vacuum and said first chamber containing a vacumm-stable viscous fluid therein; whereby, as said viscous fluid flows from said first chamber into said constant volume second chamber in response to said vacuum, said piston progressively slides in said casing from an extended position into a retracted position; and means for connecting said piston to a sryinge module for operating said syringe module as said piston advances from extended to retracted positions.

2. The power module of claim 1 in whih said casing has concentric cylindrical inner and outer walls; said second chamber being disposed within said inner wall and said first chamber being disposed between said inner and outer walls.

3. The power module of claim 2 in which said piston is annular and slidably engages opposing surfaces of said inner and outer walls.

4. The power module of claim 1 in which said viscous fluid undergoes a viscosity change at different temperatures within the operative temperature range of said module; said second chamber under partial vacumm containing a small amount of a volatitle fluid having an offsetting change in partial pressures within said operative range and being immiscible in said viscous fluid.

5. The power module of claim 1 in which said viscous fluid is polyisobutylene.

6. The power module of claim 1 in which said casing has concentric cylindrical inner and outer walls with said first chamber being disposed between said inner and outer walls and said second chamber being disposed within said inner wall; said piston being annular and slidably engaging opposing surfaces of said inner and outer walls; and detachable means temporarily joining said annular piston and casing for preventing rotation of said annular piston within said first chamber until said means is detached.

7. A syringe module adapted for connection to a power module as recited in claim 1, comprising a syringe barrel of generally cylindrical configuration having an outlet at one end for the discharge of a drug received in said barrel and having attachment means at its opposite end for irreversibly engaging the connecting means of a power module.

8. The syringe module of claim 7 in which said attachment means includes a plurality of circumferentially-spaced lugs adapted to be non-removably received in bayonet slots of a power module.

9. The syringe module of claim 8 in which said lugs are flexible and are provided with ratchet teeth.

10. The syringe module of claim 7 in which a resilient plunger is disposed within said barrel; said plunger having retraction means accessible through said opposite end of said barrel for gripping and retracting said plunger when said barrel is to be filled with a drug through said outlet.

11. The syringe module of claim 7 in which a plunger is slidably disposed within said barrel; a piercable membrane within said barrel adjacent said outlet; and a hollow needle within said barrel having a lumen communicating with said outlet and having a pointed tip for piercing said membrane as said plunger is advanced within said barrel.

12. A power module for a drug infusion devision comprising a casing having a first chamber and a second chamber and having a metering flow passage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows from said first chamber into said second chamber in response to said vacuum, said piston progressively slides in said casing from an extended position into a retracted position; means for connecting said piston to a syringe module for operating said syringe module as said piston advances from extended to retracted positions; said casing having concentric cylindrical inner and outer walls; said second chamber being disposed within said inner wall and said first chamber being disposed between said inner and outer walls; said metering flow passage comprising an opening in said inner wall; said valve means comprising a valve member movably mounted in said casing for controlling flow through said opening.

13. The power module of claim 12 in which said valve means comprises a closure member rotatably received in said inner chamber and forming an end wall for said chamber; said opening in said inner wall being in the form of an elongated slot extending in the direction of rotation of said closure member.

14. The power module of claim 13 in which said closure member also has an elongated slot extending in the direction of, and alignable with, said slot of said inner wall.

15. The power module of claim 12 in which said valve means includes a closure member rotatably received in said casing and forming a wall portion of said inner chamber; said closure member having a partition with a port extending therethrough; and vacuum integrity indicating means comprising a resilient member having a stem extending through said port and having a deformable head portion normally sealing said port and held against the external surface of said partition by atmospheric pressure; said deformable head portion assuming an altered configuration when the vacuum within said inner chamber is dissipated and atmospheric pressure no longer forcefully urges said head portion against said partition.

16. The power module of claim 15 in which said closure member includes a transparent or translucent panel engaged by said head portion and through which said head portion may be viewed when said head portion assumes said altered configuration.

17. A power module for a drug infusion device comprising a casing having a first chamber and a secodn chamber and having a metering flow pasage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows from said first chamber into said second chamber in response to said vacuum, said piston progressively slides in said casing from an extended position into a retracted position; means for connecting said piston to a syringe module for operating said syringe module as said piston advances from extended to retracted positions; said casing having concentric cylindrical inner and outer walls with said first chamber being disposed between said inner and outer walls and said second chamber being disposed within said inner wall; said piston being annular and slidably engaging opposing surfaces of said inner and outer walls; and detachable means temporarily joining said annular piston and casing for preventing rotation of said annular piston within said first chamber until said means is detached; said annular piston having an outer surface portion extending beyond said outer wall; sad means for preventing rotation of said annular piston comrpising a band of tape adhesively and removably engaging both the outer surface of said outer wall and said surface portion of said annular piston.

18. A drug infusion device having a power section and a syringe section; said power section comprising a casing having a first chamber and a second chamber and having a metering flow passage therebetween; adjustable valve means for opening and closing said passage; a piston slidably received in said casing and constituting a movable wall of said first chamber; said second chamber being of constant volume and under partial vacuum and said first chamber containing a vacuum-stable viscous fluid therein; whereby, as said viscous fluid flows through said passage from said first chamber into said constant volume second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; and means for operatively connecting said power and syringe sections to that retraction of said piston causes advancement of said syringe plunger.

19. The device of claim 18 in which said power and syringe sections constitute separate modules; said means for connecting said sections comprising interfitting portions of said sections.

20. The device of claim 19 in which said syringe section is provided with a piercable membrane within said barrel adjacent said outlet; and a hollow needle within said barrel having a lumen communicating with said outlet and having a pointed tip for piercing said membrane as said plunger is advanced within said barrel.

21. The device of claim 18 in which said casing has concentric cylindrical inner and outer walls; said second chamber being disposed within said inner wall and said first chamber being disposed between said inner and outer walls.

22. The device of claim 21 in which said piston is annular and slidably engages opposing surfaces of said inner and outer walls.

23. The device of claim 18 in which said viscous fluid undegoes a viscosity change at different temperatures within the operative temperature range of said module; said second chamber under partial vacuum containing a small amount of a volatile fluid having an offsetting change in partial pressures within said operative range and being immiscible in said viscous fluid.

24. The device fo claim 18 in which said viscous fluid is polyisobutylene.

25. The device of claim 18 in which said casing has concentric cylindrical inner and outer walls with said first chamber being disposed between said inner and outer walls and said second chamber being disposed within said inner wall; said piston being annular and slidably engaging opposing surfaces of said inner and outer walls; and detachable means temporarily joining said annular piston and casing for preventing rotation of said annular piston within said first chamber until said means is detached.

26. A drug infusion device having a power section and a syringe section; said power section comprising a casing having a first chamber and a second chamber and having a metering flow passage therebeween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said power and syringe sections constituting separate modules and said means for connecting said sections comprising interfitting portions of said sections; said interfitting portions including lugs provided by one of said sections and lug-receiving slots provided by the other of said sections.

27. The device of claim 26 in which said lugs are provided by said syringe barrel at one end thereof and said slots are provided by said piston of said power section.

28. The device of claim 26 in which at least one of said lugs and piston have ratchet teeth for preventing disengagement following coupling of said sections.

29. A drug infusion device having a power section and a syring section; said power section comprising a casing having a first chamber and a second chamber and having a metering flow passage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said power and syringe sections constituting separate modules; said means for connecting said sections comprising interfitting portions of said sections; said power unit including a portion of said casing that engages the plunger of said syringe, and advances said plunger a limited distance to discharge a bolus of drug from said barrel, as said sections are connected together.

30. A drug infusion device having a power section and a syring section; said power section comprising a casing having a first chamber and a second chamber and having a metering flow passage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said power and syringe sections constituting separate modules; and means for connecting said sections comprising interfitting portions of said sections; said syringe section being provided with a piercable membrane within said barrel adjacent said outlet; and a hollow needle within said barrel having a lumen communicating with said outlet and having a pointed tip for piercing said membrane as said plunger is advanced within said barrel; said power unit including a portion of said casing that engages the plunger of said syringe, and advances said plunger a limited distance to cause piercing of said membrane by a needle and a discharging of a bolus of drug from said barrel, as said sections are conected together.

31. A drug infusion device having a power section and a syringe section; said power section comprising a casing having a first chamber and a second chamber and having a metering flow passage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said casing having concentric inner and outer walls; said second chamber being disposed within said inner wall and said first chamber being disposed between said inner and outer wals; said piston being annular and slidably engaging opposing surfaces of said inner and outer walls; said metering passage comprising an opening in said inner wall; said valve means comprising a valve member movably mounted in said casing for controlling flow through said opening.

32. The device of claim 31 in which said valve means includes a closure member rotatably received in said casing and forming a wall portion of said inner chamber; said closure member having a partition with a port extending therethrough; and vacuum integrity indicating means comprising a resilient member having a deformable head portion normally sealing said port and held against the external surace of said partition by atmospheric pressure; said deformable head portion assuming an altered configuration when the vacuum within said inner chamber is dissipated and atmospheric pressure no longer forcefully urges said head portion against said partition.

33. The device of claim 32 in which said closure member includes a transparent or translucent panel engaged by said head portion and through which said head portion may be viewed when said head portion assumes said altered configuration.

34. A drug infusion device having a power section and a syringe section; said power section comprising a casing having a first chamber and a second chamber and having a metering flow paassage therebetween; adjustable valve means for opening and closing said passage; a piston slidably received in said casing and constituting a movable wall of said first chamber; said second chamber being under partial vacuum and said first chamber containing a vacuum-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said casing having concentric inner and outer walls; said second chamber being disposed within said inner wall and said first chamber being disposed between said inner and outer walls; said piston being annular and slidably engaging opposing surfaces of said inner and outer walls; said valve means comprising a closure member rotatably received in said inner chamber and forming an end wall for said chamber; said opening in said inner wall being in the form of an elongated slot extending in the direction of rotation of said closure member.

35. The device of claim 34 in which said closure member also has an elongated slot extending in the direction of, and alignable with, said slot of said inner wall.

36. A drug infusion device having a power section and a syringe section; said power section comprising a casing having a first chamber and a second chamber and having a metering flow passage therebetween; adjustable valve means for opening and closing said passage; a piston slidably received in said casing and constituting a movable wall of said first chamber; said second chamber being under partial vacuum and said first chamber containing a vacumm-stable viscous fluid therein; whereby, as said viscous fluid flows through said passage from said first chamber into said second chamber in response to said vacuum, said piston progressively slides in said casing from an extended position into a retracted position; said syringe section including a barrel for containing a liquid drug to be infused, an outlet for discharge of said drug from said barrel, and a plunger slidably received within said barrel and capable of being advanced within said barrel to displace drug therefrom; means for operatively connecting said power and syringe sections so that retraction of said piston causes advancement of said syringe plunger; said casing having concentric cylindrical inner and outer walls with said first chamber being disposed between said inner and outer walls and said second chamber being disposed within said inner wall; said piston being annular and slidably engaging opposing surfaces of said inner and outer walls; detachable means temporarily joining said annular piston and casing for preventing rotation of said annular piston within said first chamber until said means is detached; said annular piston having an outer surface portion extending beyond said outer wall; said means for preventing rotation of said annular piston comprising a band of tape adhesively and removably engaging both the outer surface of said outer wall and said surface portion of said annular piston.

* * * * *